(12) United States Patent
Madej et al.

(10) Patent No.: US 12,714,456 B2
(45) Date of Patent: Aug. 25, 2026

(54) ASPIRATION CATHETER WITH DISTALLY DIRECTED FLUID JET

(71) Applicant: Boston Scientific Scimed, Inc., Maple Grove, MN (US)

(72) Inventors: Alyssa Madej, Minnetonka, MN (US); Cass Alexander Hanson, St. Paul, MN (US); Michael P Schrom, Forest Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 21 days.

(21) Appl. No.: 18/415,797

(22) Filed: Jan. 18, 2024

(65) Prior Publication Data

US 2024/0245423 A1 Jul. 25, 2024

Related U.S. Application Data

(60) Provisional application No. 63/440,261, filed on Jan. 20, 2023.

(51) Int. Cl.
*A61B 17/3203* (2006.01)
*A61B 17/22* (2006.01)
*A61M 25/00* (2006.01)

(52) U.S. Cl.
CPC .................. *A61B 17/32037* (2013.01); *A61B 2017/22079* (2013.01); *A61M 25/007* (2013.01)

(58) Field of Classification Search
None
See application file for complete search history.

(56) References Cited

U.S. PATENT DOCUMENTS 2,568,566 A 9/1951 Edward
5,370,609 A 12/1994 Drasler et al.
(Continued)

FOREIGN PATENT DOCUMENTS

EP 2362751 B1 9/2016
EP 2120737 B1 4/2020
(Continued)

OTHER PUBLICATIONS

International Search Report and Written Opinion dated Mar. 25, 2024 for International Application No. PCT/US2024/011916.

*Primary Examiner* — Shaun L David
(74) *Attorney, Agent, or Firm* — Seager Tufte & Wickhem, LLP

(57) ABSTRACT

Thrombectomy catheter and high-pressure systems for preventing clogging of a thrombectomy catheter. An illustrative thrombectomy catheter may comprise a catheter body including a catheter lumen extending therethrough. A high-pressure fluid supply tube extends through the catheter lumen from the catheter body proximal end region toward the catheter body distal end region. The high-pressure fluid supply tube is configured for communication with a fluid source near the catheter body proximal end region. The high-pressure supply tube includes at least one proximally projecting jet orifice for expelling at least one proximally oriented fluid jet from said high-pressure fluid supply tube in a generally proximal direction and at least one distally projecting jet orifice for expelling at least one distally oriented fluid jet from said high-pressure fluid supply tube in a generally distal direction. The catheter body further includes an entrainment inflow orifice positioned along the catheter distal portion.

16 Claims, 6 Drawing Sheets

(56) References Cited

U.S. PATENT DOCUMENTS 5,425,723 A 6/1995 Wang
5,785,675 A 7/1998 Drasler et al.
5,976,103 A 11/1999 Martin
5,989,210 A 11/1999 Morris et al.
5,989,271 A 11/1999 Bonnette et al.
6,096,001 A 8/2000 Drasler et al.
6,129,697 A 10/2000 Drasler et al.
6,224,570 B1 5/2001 Le et al.
6,258,061 B1 7/2001 Drasler et al.
6,471,683 B2 10/2002 Drasler et al.
6,544,209 B1 4/2003 Drasler et al.
6,558,366 B1 5/2003 Drasler et al.
6,676,627 B1 1/2004 Bonnette et al.
6,676,637 B1 1/2004 Bonnette et al.
6,719,718 B2 4/2004 Bonnette et al.
6,755,803 B1 6/2004 Le et al.
6,764,483 B1 7/2004 Bonnette et al.
6,805,684 B2 10/2004 Bonnette et al.
6,875,193 B1 4/2005 Bonnette et al.
6,926,726 B2 8/2005 Drasler et al.
6,932,828 B2 8/2005 Bonnette et al.
6,945,951 B1 9/2005 Bonnette et al.
6,984,239 B1 1/2006 Drasler et al.
7,056,315 B2 6/2006 Gonon et al.
7,220,269 B1 5/2007 Ansel et al.
7,226,433 B2 6/2007 Bonnette et al.
7,486,175 B2 2/2009 Suzuki et al.
7,572,244 B2 8/2009 Weisel et al.
7,615,031 B2 11/2009 Bonnette et al.
7,842,010 B2 11/2010 Bonnette et al.
7,846,175 B2 12/2010 Bonnette et al.
7,879,022 B2 2/2011 Bonnette et al.
7,935,077 B2 5/2011 Kneip et al.
7,951,161 B2 5/2011 Bonnette et al.
7,996,974 B2 8/2011 Kozak et al.
8,012,117 B2 9/2011 Bonnette et al.
8,162,877 B2 4/2012 Bonnette et al.
8,162,878 B2 4/2012 Bonnette et al.
8,303,538 B2 11/2012 Bonnette et al.
8,353,858 B2 1/2013 Kozak et al.
8,430,837 B2 4/2013 Jenson et al.
8,439,878 B2 5/2013 Bonnette et al.
8,475,487 B2 7/2013 Bonnette et al.
8,491,523 B2 7/2013 Scherger, III et al.
8,597,238 B2 12/2013 Bonnette et al.
8,647,294 B2 2/2014 Bonnette et al.
8,657,777 B2 2/2014 Kozak et al.
8,857,734 B2 10/2014 Kojima
8,900,179 B2 12/2014 Jenson et al.
8,998,843 B2 4/2015 Bonnette et al.
9,078,691 B2 7/2015 Morris et al.
9,510,854 B2 12/2016 Mallaby
9,662,137 B2 5/2017 Jenson et al.
9,833,257 B2 12/2017 Bonnette et al.
9,883,877 B2 2/2018 Look et al.
10,004,846 B2 6/2018 Bonnette et al.
10,314,608 B2 6/2019 Jenson et al.
10,492,805 B2 12/2019 Culbert et al.
10,499,944 B2 12/2019 Mallaby
10,561,440 B2 2/2020 Look et al.
10,716,583 B2 7/2020 Look et al.
11,497,521 B2 11/2022 Mallaby
11,653,945 B2 5/2023 Jenson et al.
11,678,905 B2 6/2023 Look et al.
11,931,060 B2 3/2024 Hanson et al.
11,969,176 B2 4/2024 Quillin
12,150,659 B2 11/2024 Look et al.
12,171,445 B2 12/2024 Culbert et al.
2005/0096607 A1 5/2005 Beck
2006/0106285 A1 5/2006 Boulais et al.
2006/0129091 A1 6/2006 Bonnette et al.
2008/0188793 A1 8/2008 Kozak et al.
2008/0275383 A1 11/2008 Weisel et al.
2008/0275393 A1 11/2008 Bonnette et al.
2008/0319386 A1 12/2008 Bonnette et al.
2011/0015564 A1 1/2011 Bonnette et al.
2013/0046282 A1 2/2013 O'Day et al.
2013/0310845 A1 11/2013 Scherger, III et al.
2014/0005699 A1 1/2014 Bonnette et al.
2014/0088610 A1 3/2014 Bonnette et al.
2014/0155830 A1* 6/2014 Bonnette ........... A61M 25/0026 604/150
2014/0214060 A1 7/2014 Bonnette et al.
2014/0228869 A1 8/2014 Bonnette et al.
2014/0277006 A1 9/2014 Bonnette et al.
2017/0290598 A1 10/2017 Culbert et al.
2018/0207397 A1 7/2018 Look et al.
2018/0228502 A1 8/2018 Shaffer et al.
2019/0209745 A1 7/2019 Hanson et al.
2019/0274704 A1 9/2019 Jenson et al.
2020/0015840 A1 1/2020 Mallaby
2020/0022711 A1 1/2020 Look et al.
2020/0121356 A1 4/2020 Look et al.
2020/0155178 A1 5/2020 Culbert et al.
2020/0297363 A1 9/2020 Look et al.
2022/0370084 A1 11/2022 Quillin
2022/0387065 A1 12/2022 Mallaby
2024/0245422 A1 7/2024 Madej et al.
2024/0245423 A1 7/2024 Madej et al.
2025/0143723 A1 5/2025 Tassoni, Jr. et al.

FOREIGN PATENT DOCUMENTS

EP 3689274 A1 8/2020
EP 3145557 B1 1/2021
EP 3821921 A1 5/2021
EP 3570901 B1 5/2022
JP 5385155 B2 1/2014
JP 2019513452 A 5/2019
WO 0151116 A2 7/2001
WO 2008097339 A2 8/2008
WO 2008097993 A2 8/2008
WO 2017041062 A1 3/2017
WO 2017177022 A1 10/2017
WO 2019140132 A1 7/2019

* cited by examiner 400
404
402
406
408
410
412
414
416
418a
418b
418c
418d
420a
420b
420c
420d

ASPIRATION CATHETER WITH DISTALLY DIRECTED FLUID JET

CROSS-REFERENCE TO RELATED APPLICATIONS

This application claims the benefit of U.S. Provisional Patent Application Ser. No. 63/440,261, filed Jan. 20, 2023, which is incorporated herein by reference.

TECHNICAL FIELD

The disclosure is directed to thrombectomy systems. More particularly, the disclosure is directed to an aspiration catheter system for improved clot removal. In some instances, the aspiration catheter may include a distally directed fluid jet proximate the distal end of the aspiration catheter.

BACKGROUND

Thrombectomy is a procedure for removing thrombus from the vasculature of a patient. Mechanical and fluid-based systems can be used to remove thrombus. With fluid-based systems, an infusion fluid may be infused to a treatment area of a vessel with a catheter to dislodge the thrombus. In some instances, an effluent (e.g., the infusion fluid and/or blood) including the dislodged thrombus may be extracted from the vessel through the catheter. Of the known thrombectomy systems and methods, there is an ongoing need to provide alternative configurations of thrombectomy catheters and systems, as well as methods of operating such thrombectomy systems.

SUMMARY

This disclosure provides design, material, manufacturing method, and use alternatives for medical devices.

In a first example, a thrombectomy catheter may comprise a catheter body extending from a proximal end region to a distal end region and including a catheter lumen extending between the proximal end region and the distal end region, a high-pressure fluid supply tube extending through the catheter lumen from the catheter body proximal end region toward the catheter body distal end region, the high-pressure fluid supply tube configured for communication with a fluid source near the catheter body proximal end region, at least one proximally projecting jet orifice for expelling at least one proximally oriented fluid jet from said high-pressure fluid supply tube within the catheter lumen in a generally proximal direction, at least one distally projecting jet orifice for expelling at least one distally oriented fluid jet from said high-pressure fluid supply tube within the catheter lumen in a generally distal direction, and an entrainment inflow orifice positioned along the catheter distal portion.

Alternatively or additionally to any of the examples above, in another example, the at least one distally projecting jet orifice may be distal to the at least one proximally projecting jet orifice.

Alternatively or additionally to any of the examples above, in another example, the at least one distally oriented fluid jet may impinge an inner surface of the catheter body.

Alternatively or additionally to any of the examples above, in another example, the at least one distally projecting jet orifice may extend through a circumferential sidewall of the high-pressure fluid supply tube.

Alternatively or additionally to any of the examples above, in another example, the at least one distally projecting jet orifice may be axially aligned with the at least one proximally projecting jet orifice.

Alternatively or additionally to any of the examples above, in another example, the at least one distally projecting jet orifice may be circumferentially offset from the at least one proximally projecting jet orifice.

Alternatively or additionally to any of the examples above, in another example, the at least one distally projecting jet orifice may be circumferentially offset from the at least one proximally projecting jet orifice by in the range of about 45° to about 135°.

Alternatively or additionally to any of the examples above, in another example, the sidewalls of the at least one distally projecting jet orifice extends at an obtuse angle relative to a longitudinal axis of the high-pressure fluid supply tube.

Alternatively or additionally to any of the examples above, in another example, the at least one distally projecting jet orifice may extend through a distal end of the high-pressure fluid supply tube.

Alternatively or additionally to any of the examples above, in another example, the at least one distally projecting jet orifice may be in line with a longitudinal axis of the high-pressure fluid supply tube.

Alternatively or additionally to any of the examples above, in another example, a diameter of the at least one distally projecting jet orifice may be less than an inner diameter of the high-pressure fluid supply tube.

Alternatively or additionally to any of the examples above, in another example, a diameter of the at least one distally projecting jet orifice may be approximately the same as an inner diameter of the high-pressure fluid supply tube.

Alternatively or additionally to any of the examples above, in another example, the sidewalls of the at least one proximally projecting jet orifice may extend at an acute angle relative to a longitudinal axis of the high-pressure fluid supply tube.

Alternatively or additionally to any of the examples above, in another example, the at least one distally projecting jet orifice may comprise two or more distally projecting jet orifices.

Alternatively or additionally to any of the examples above, in another example, the at least one proximally projecting jet orifice may comprise two or more proximally projecting jet orifices.

In another example, a thrombectomy catheter may comprise a catheter body extending from a proximal end region to a distal end region and including a catheter lumen extending between the proximal end region and the distal end region, a high-pressure fluid supply tube extending through the catheter lumen from the catheter body proximal end region toward the catheter body distal end region, the high-pressure fluid supply tube configured for communication with a fluid source near the catheter body proximal end region, at least one proximally projecting jet orifice for expelling at least one proximally oriented fluid jet from said high-pressure fluid supply tube within the catheter lumen in a generally proximal direction, at least one distally projecting jet orifice extending through a circumferential sidewall of the high-pressure supply tube, the at least one distally projecting orifice for expelling at least one distally oriented fluid jet from said high-pressure fluid supply tube within the catheter lumen in a generally distal direction, and an entrainment inflow orifice positioned along the catheter distal portion. The at least one distally oriented fluid jet may be configured to impinge an inner surface of the catheter body.

Alternatively or additionally to any of the examples above, in another example, the at least one distally projecting jet orifice may be axially aligned with the at least one proximally projecting jet orifice.

Alternatively or additionally to any of the examples above, in another example, the at least one distally projecting jet orifice may be circumferentially offset from the at least one proximally projecting jet orifice.

In another example, a thrombectomy catheter may comprise a catheter body extending from a proximal end region to a distal end region and including a catheter lumen extending between the proximal end region and the distal end region, a high-pressure fluid supply tube extending through the catheter lumen from the catheter body proximal end region toward the catheter body distal end region, the high-pressure fluid supply tube configured for communication with a fluid source near the catheter body proximal end region, at least one proximally projecting jet orifice for expelling at least one proximally oriented fluid jet from said high-pressure fluid supply tube within the catheter lumen in a generally proximal direction, at least one distally projecting jet orifice extending through a distal end of the high-pressure fluid supply tube, the at least one distally projecting orifice for expelling at least one distally oriented fluid jet from said high-pressure fluid supply tube within the catheter lumen in a generally distal direction and an entrainment inflow orifice positioned along the catheter distal portion. The at least one distally projecting jet orifice may extend generally orthogonal to a longitudinal axis of the high-pressure supply tube.

Alternatively or additionally to any of the examples above, in another example, a diameter of the at least one distally projecting jet orifice may be less than an inner diameter of the high-pressure fluid supply tube.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
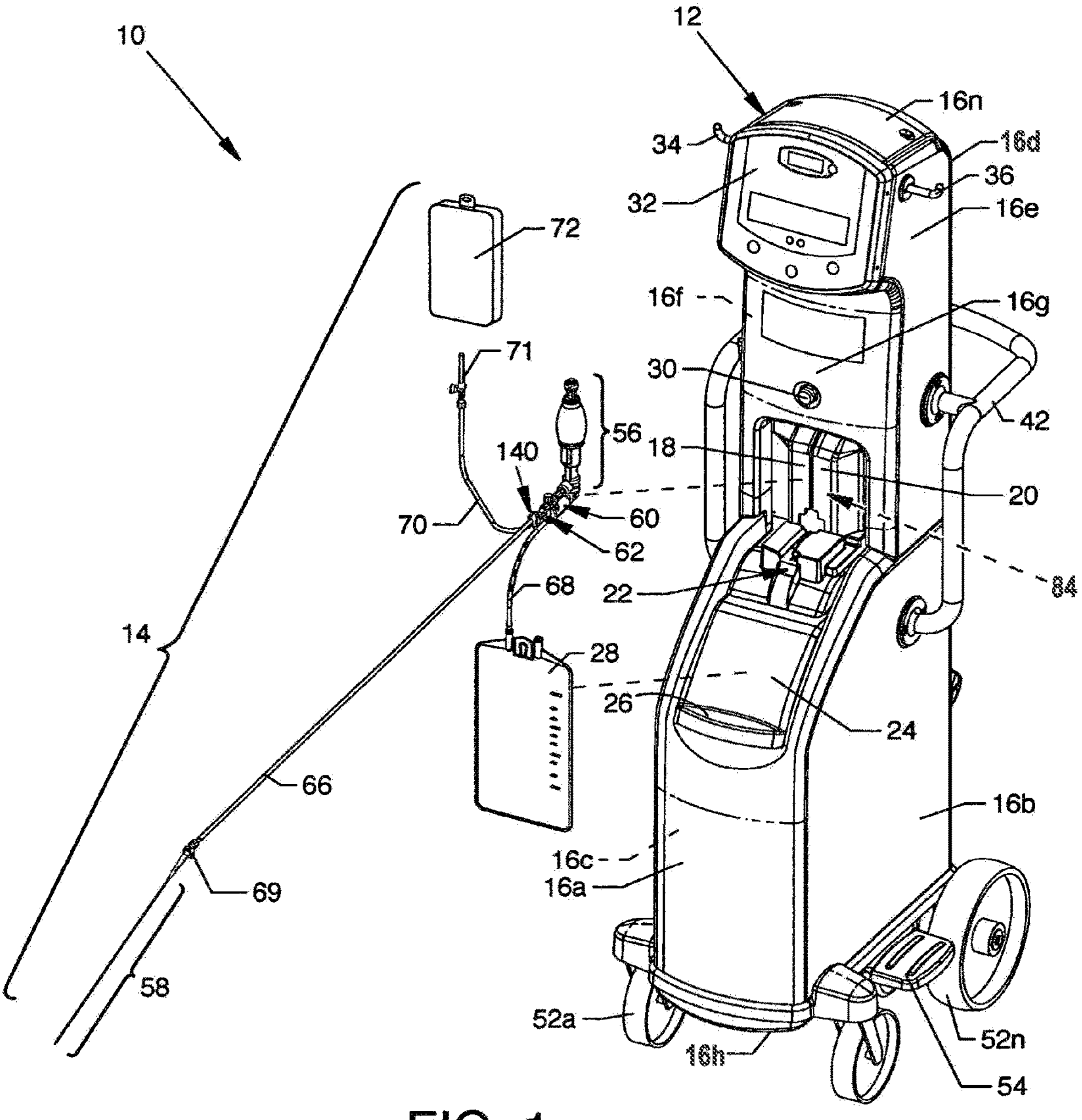
FIG. 1 is a perspective view of an illustrative thrombectomy system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Thrombectomy catheters and systems may be used to remove thrombus, plaques, lesions, clots, etc. from veins or arteries. Some thrombectomy catheters may use a jet tube that is configured in a way that the jets point directly backward (i.e., proximally into the catheter (e.g., parallel to the shaft walls) to prevent shaft damage. However, this jet tube design may block a significant portion of the cross-sectional area of the aspiration lumen, which may in turn, decrease aspiration rates. Further this type of jet orientation may require a side window or port which may limit the vessel diameter that the device is able to reach due to the risk of the vessel wall being pulled into the catheter side window or port as well as increasing the presence of hemolysis in the target vessels. Other jet aspiration catheters may utilize high velocity saline jets in a series to entrain fluid or clot material into and through the shaft of the catheter. While proximally facing jets may macerate any clot the jetted fluid may come into contact with and prevent clogging along a length of the catheter shaft, the distal tip of the catheter may still become clogged. The distal tip of the catheter may be at greater risk of clogging during the treatment of subacute or chronic clots. Disclosed herein are a variety of high-pressure supply tubes provided with a thrombectomy catheter which greatly reduce or eliminate the changes of clogging at the distal tip of the catheter and help to remove the clot more quickly.

FIG. 1 is a perspective view of an illustrative thrombectomy system 10. The thrombectomy system 10 may include a control console or drive unit 12 and a pump/catheter assembly 14. In some instances, the pump/catheter assembly 14 may be a single use device in which a new pump/catheter assembly 14 may be used with the drive unit 12 for each medical procedure. Shown on the drive unit 12 are a plurality of removable panels 16*a*-16*n* about and along the drive unit 12 enclosing the internal structure of the drive unit 12. An illustrative drive unit 12 is described in commonly assigned U.S. Pat. No. 7,935,077, titled THROMBECTOMY CATHETER DEPLOYMENT SYSTEM, the disclosure of which is hereby incorporated by reference. Centrally located in the drive unit 12 and aligned to the lower region of the panel 16*g* may be automatically opening doors 18 and 20 which open to expose the interior of the drive unit 12 to provide access to a carriage assembly 22. The carriage assembly 22, which may accommodate components of the pump/catheter assembly 14, as discussed further herein, is shown accessible via opening the closed doors 18 and 20. The drive unit 12 may include a catch basin for collecting fluid leakage from the components of the pump/catheter assembly 14. For example, a removable drip tray 24 is shown located on the front of the drive unit 12 extending from below the carriage assembly 22 toward the panel 16*a*. Other configurations of catch basins are also contemplated. The drip tray 24 and a removable receptacle 26 may collectively support and accommodate an effluent collection bag, such as effluent collection bag 28 of the pump/catheter assembly 14. In other instances, the drive unit 12 may include a different structure, such as a hook for hanging the effluent collection bag 28 from, or a shelf for setting the effluent collection bag 28 on. In instances where the carriage assembly 22 is movable, a carriage assembly activation switch 30 may be provided with the drive unit 12, such as located on panel 16*g*, to selectively position the carriage assembly 22 inwardly or outwardly. A user interface 32, including memory capabilities, may be provided with the drive unit 12, such as located at the upper region of the drive unit 12 between the upper regions of the upper side panels 16*e* and 16*f*. Saline bag hooks 34 and 36 may extend through the panels 16*e* and 16*f* to hang saline bags therefrom. The drive unit 12 may include a handle 42 as well as a plurality of wheels 52*a*-52*n* and brake pedals 54 for wheel lockage to assist in maneuvering the drive unit 12 by medical personnel.

The pump/catheter assembly 14, which may be a disposable single-use device, is shown unattached from the drive unit 12. The pump/catheter assembly 14 includes a pump 56 and a thrombectomy catheter 58. During use, a portion of the pump/catheter assembly 14 may be secured within a portion of the drive unit 12. Other components included in the pump/catheter assembly 14 may include a bubble trap 60 attached to the pump 56, a connection manifold assembly 62 connected to the bubble trap 60, an effluent return tube 66 connected between the connection manifold assembly 62 and the thrombectomy catheter 58, a high-pressure fluid supply tube 64 attached between the output of the pump 56 and the thrombectomy catheter 58 which may be coaxially arranged inside the effluent return tube 66, a transition fixture 69 between the distal end of the effluent return tube 66 and the proximal end of the thrombectomy catheter 58, an effluent waste tube 68 connecting the effluent collection bag 28 to the connection manifold assembly 62, and a fluid supply tube 70 having a bag spike 71 connecting a fluid supply bag 72 (e.g., a saline bag) to the connection manifold assembly 62. The fluid supply tube 70 may be in fluid communication with the interior of the bubble trap 60 to provide fluid from the fluid supply bag 72 to the pump 56 and then to the thrombectomy catheter 58 through the high-pressure fluid supply tube 64.

Figure 2:
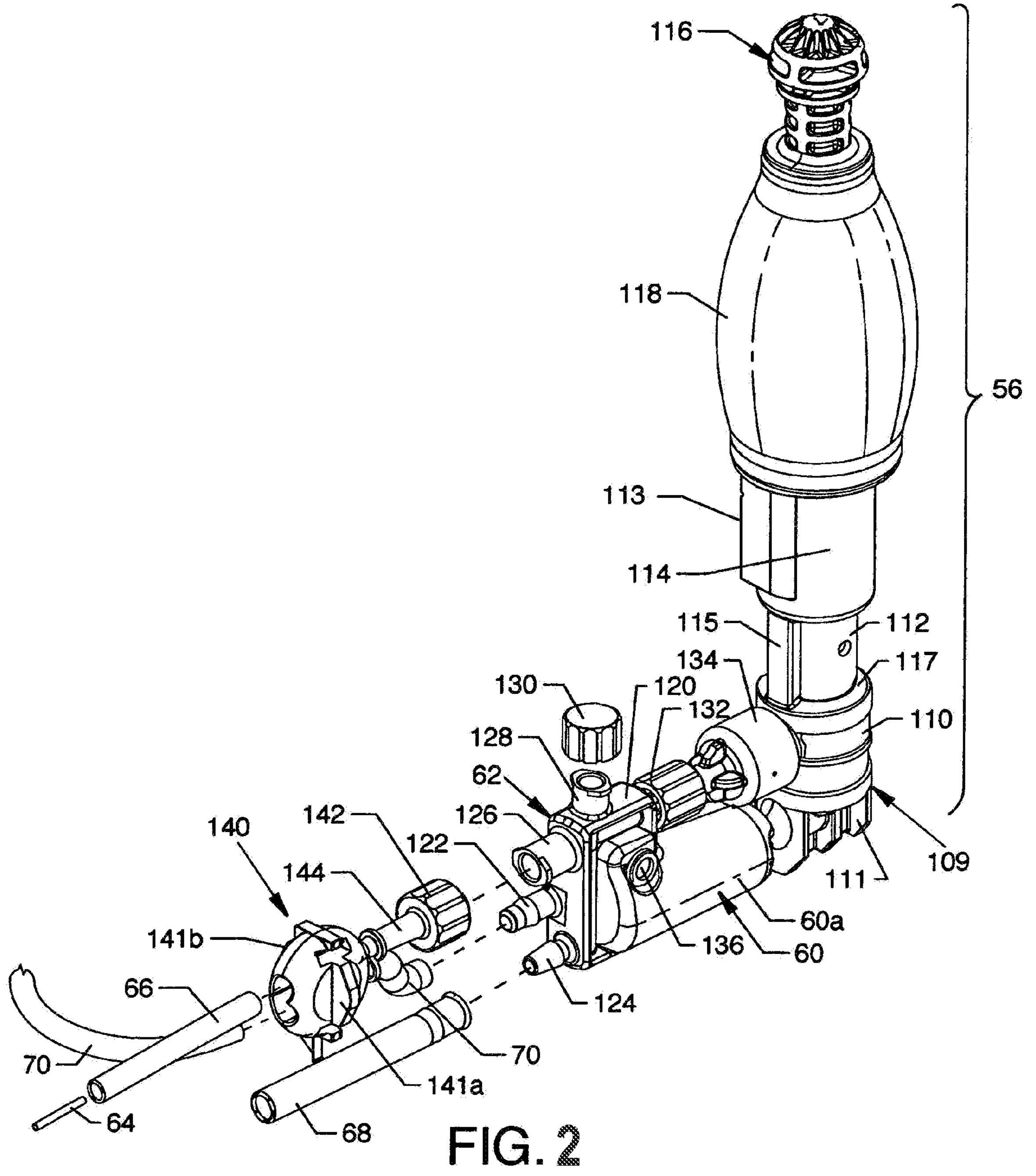
FIG. 2 is a partially exploded perspective view of the pump, the bubble trap, the connection manifold assembly, and an associated fixture of the pump/catheter assembly for use in the thrombectomy system of FIG. 1.

FIG. 2 is a partially exploded perspective view of several components of the pump/catheter assembly 14 generally including the pump 56, the bubble trap 60, the connection manifold assembly 62, and a fixture 140. The pump 56 centers about a tubular body 112. Components are located about the lower region of the tubular body 112 and include a base 109 having an upper portion 110 and a lower portion 111 both positioned about the lower region of the tubular body 112. An annular surface 117 is included at the top of the upper portion 110 of the base 109 for intimate contact with capture tabs of the carriage assembly 22 to contain the pump 56 within the carriage assembly 22. A top body 114, is positioned about the upper region of the tubular body 112. The base 109 and the top body 114, as well as a connecting panel 115, may be molded or otherwise suitably constructed to encompass the greater part of the tubular body 112, for example. A data plate 113 may also be included on the top body 114 for the inclusion of a barcode, an RFID tag, or other informational displays to determine operational parameters of the device.

Figure 3:
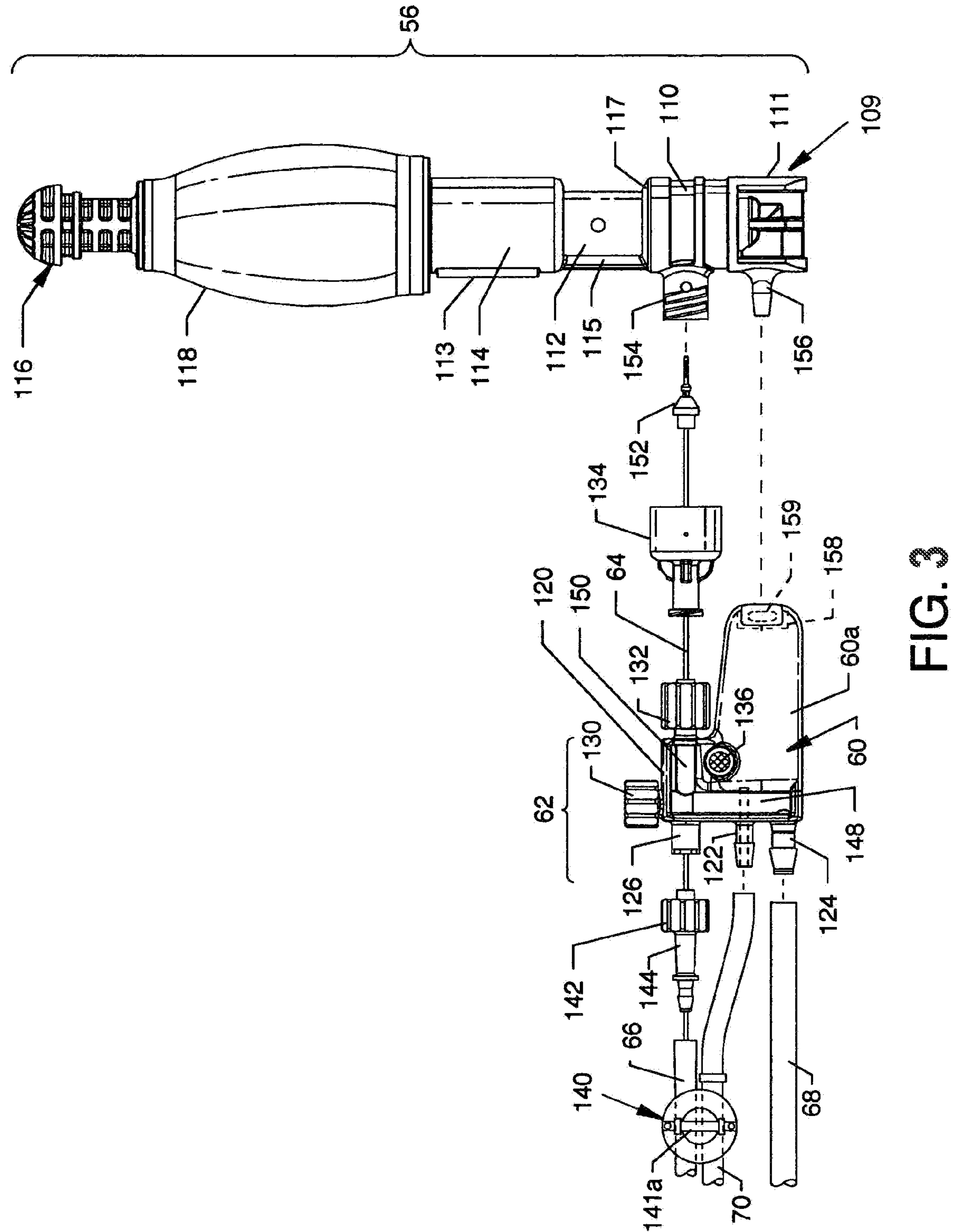
FIG. 3 is a partially exploded side view of the pump, the bubble trap, the connection manifold assembly, and associated fixture of the pump/catheter assembly for use in the thrombectomy system of FIG. 1.

The pump 56 may include a hemispherically-shaped pump piston head 116 having a flexible boot 118 connected to and extending between the top body 114 and the pump piston head 116. In some instances, the geometrically configured lower portion 111 of the base 109 may serve as a mount for one end of the bubble trap 60 (FIG. 3).

The connection manifold assembly 62 may be secured directly to the other end of the bubble trap 60 and in some instances may include a bracket 120 to which is attached a vertically oriented tubular manifold 148 having a plurality of ports attached or formed therethrough including a fluid (e.g., saline) inlet port 122, an effluent outlet port 124, a Luer style effluent return port 126, and/or an auxiliary port 128 and cap 130. Also shown are connectors 132 and 134 connectingly extending between the connection manifold assembly 62 and the upper portion 110 of the base 109.

The bubble trap 60 may include mating halves of which one mating half 60*a* is shown. A hydrophobic filter 136 may be included at the upper forward region of the bubble trap half 60*a*. Another hydrophobic filter may be included on the second bubble trap half (not explicitly shown) which opposes the hydrophobic filter 136 on the bubble trap half 60*a*.

The fixture 140, and components associated therewith, assists in support and connection of the effluent return tube 66 to the effluent return port 126 by a connector 142 combined continuously with a connection tube 144, and also assists in support, passage and connection of the fluid supply tube 70 with the fluid inlet port 122. The fixture 140 may include outwardly extending vertically aligned and opposed tabs 141*a* and 141*b* which prevent the fixture 140 and associated effluent return tube 66 containing the high-pressure fluid supply tube 64 and the fluid supply tube 70 from contacting a roller pump (not explicitly shown) provided with the drive unit 12, such as located in the carriage assembly 22 or adjacent thereto.

FIG. 3 is a partially exploded side view of the elements of FIG. 2 illustrating the relationship of the pump 56, the bubble trap 60, the connection manifold assembly 62, and the fixture 140. Also shown is the vertically oriented tubular manifold 148 secured to the bracket 120. The effluent outlet port 124 may be connected to and in fluid communication with the lower interior of the tubular manifold 148. The effluent return port 126 may be connected to and in fluid communication with the upper interior of the tubular manifold 148. Also connecting to the tubular manifold 148 is a horizontally aligned passage port 150 and associated connector 132, each opposing the effluent return port 126. The passage port 150 may accommodate the high-pressure fluid supply tube 64 which extends distally through the lumen (not explicitly shown) of the passage port 150, the connector 132, the upper region of the tubular manifold 148, the effluent return port 126, the connector 142, the connection tube 144, and into and through the effluent return tube 66 to connect to the thrombectomy catheter 58 (FIG. 1). The proximal end of the high-pressure fluid supply tube 64 includes a high-pressure fitting 152 located near the proximal end of the high-pressure fluid supply tube 64 to facilitate connection of the high-pressure fluid supply tube 64 in fluid communication with the interior of the pump 56. The proximal end of the high-pressure fluid supply tube 64, which is the inlet to the high-pressure fluid supply tube 64, may include a plurality of very small holes (not shown) comprising a filter at the proximal end thereof. The connector 134, which may have internal and/or external threads, may be aligned over and about the high-pressure fluid supply tube 64 distal to the high-pressure fitting 152 and threadingly engage a threaded connection port 154 extending horizontally from the upper portion 110 of the base 109 of the pump 56. The connector 134 may be rotated to threadably engage the high-pressure fitting 152 with a corresponding mating threaded structure provided with the pump 56. A connector 132 may be utilized to engage the externally threaded end of the connector 134 to secure the connector 134, and thus the pump 56, to the connection manifold assembly 62 and to provide for fixation of the bubble trap 60 to the pump 56. In addition, direct connection and fluid communication between the pump 56 and the bubble trap 60 may be provided by a horizontally oriented pump fluid inlet port 156 which engages a corresponding receptor port 158 and seal 159 interior to one end of the bubble trap 60. The fluid inlet port 122 located on the bracket 120 may extend behind the tubular manifold 148 to communicate with the interior of the bubble trap 60 for fluid (e.g., saline) debubbling, whereby unpressurized fluid (e.g., saline) is made available for use by the pump 56.

Figure 4:
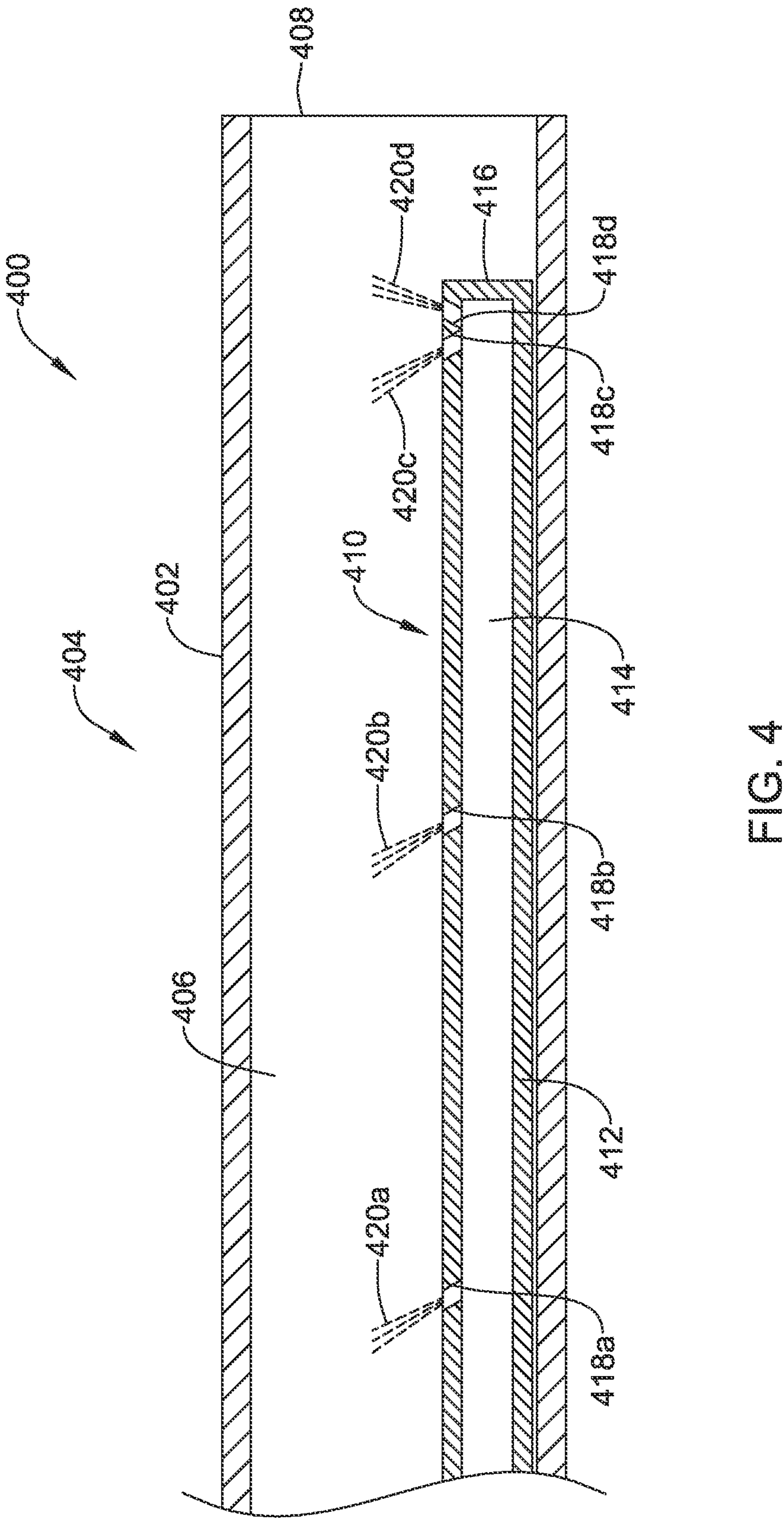
FIG. 4 is a longitudinal cross-sectional view of a distal end region of an illustrative thrombectomy catheter.

FIG. 4 is a cross-sectional view of a distal end region 404 of an illustrative thrombectomy catheter 400. The thrombectomy catheter 400 may be one illustrative example of the thrombectomy catheter 58 described above. The thrombectomy catheter 400 may include a tubular member or catheter body 402 extending from a proximal end region (not explicitly shown) configured to remain outside the body to a distal end region 404. The catheter body 402 may be one illustrative example of, or be in fluid communication with, the effluent return tube 66 of the thrombectomy catheter 58 described above. A lumen 406 may extend from the proximal end region to the distal end region 404 of the catheter body 402. The catheter body 402 may terminate at a distally facing distal opening 408 at the distal end of the catheter body 402. In some instances, the distal opening 408 may be in a plane that extends generally orthogonal to a longitudinal axis of the catheter body 402. In other instances, the distal opening 408 may be in a plane that extends generally oblique to a longitudinal axis of the catheter body 402. Generally, the distal opening 408 may be an entrainment inflow orifice. While not explicitly shown, the catheter body 402 may include one or more markers (e.g., radiopaque marker bands) disposed along the catheter body 402. Further, while not explicitly shown, in some embodiments, the catheter body 402 may include one or more openings extending through a sidewall thereof, if desired.

The thrombectomy catheter 400 may further include a high-pressure fluid supply tube 410. The high-pressure fluid supply tube 410 may be one illustrative example of, or be in fluid communication with, the high-pressure fluid supply tube 66 of the thrombectomy catheter 58 described above. The high-pressure fluid supply tube 410 may be disposed within and extend through the lumen 406 of the catheter body 402. The high-pressure fluid supply tube 410 may include a supply tube wall 412 defining a lumen or fluid pathway 414 extending therethrough. In at least some instances, the high-pressure fluid supply tube 410 may have a closed distal end 416. Because of this, fluid may be able to pass distally through the fluid pathway 414 but does not exit the distal end. The high-pressure fluid supply tube 410 may extend along a length of the catheter body 402 with the distal end 416 located within the lumen 406 of the catheter body 402 proximal to the distal opening 408 at the distal end of the catheter body 402. A proximal end of the high-pressure fluid supply tube 410 may be in fluid communication with the pump 56 described herein, to provide high-pressure fluid to the fluid pathway 414 of the high-pressure fluid supply tube 410.

A plurality of jet orifices 418*a-d* (collectively, 418) may be defined along the supply tube wall 412. For example, the supply tube wall 412 may include two, three, four, five, six, or more jet orifices 418. The jet orifices 418 may be spaced along the supply tube wall 412 at any desired intervals. For example, each of the jet orifices 418 may be equidistantly spaced from adjacent jet orifices 418 along the length of the supply tube wall 412. In other instances, the jet orifices 418 may be arranged such that the spacing between adjacent jet orifices 418 near the distal end of the supply tube wall 412 is closer than the spacing between adjacent jet orifices 418 near the proximal end of the supply tube wall 412. For instance, the spacing between the orifices 418 may gradually increase as you move proximally along the length of the shaft, or the spacing may increase in a step-wise configuration. In some instances, some or all of the jet orifices 418 may be axially aligned along the supply tube wall 412. In other instances, one or more of the jet orifices 418 may be circumferentially offset from one another about the supply tube wall 412. A number of patterns are contemplated including a helical pattern, a pattern where no two jet orifices 418 are disposed at the same axial location, a regular pattern including two or more jet orifices 418 disposed at the same axial location, an irregular pattern (where some of the jet orifices 418 may or may not be disposed at the same axial location), etc.

The jet orifices 418 may be formed using a suitable method such as electron discharge machining, etching, cutting (e.g., including laser cutting), or the like. In some instances, one or more of the jet orifices 418 may have a substantially round shape. In other instances, one or more of the jet orifices 418 may have a substantially non-round shape (e.g., oval, polygonal, irregular, etc.). In some instances, the jet orifices 418 may be beveled or otherwise include a beveled surface. It is contemplated that a size and/or a shape of the jet orifices 418 may be varied to vary the velocity of the fluid exiting the jet orifices. For example, decreasing the size of the jet orifices 418 may increase the velocity of the fluid exiting the jet orifices 418. In some embodiments, the size of the jet orifices 418 may be varied based on the pressure capacity of the thrombectomy system, the number of jet orifices, the dimensions of the high-pressure fluid supply tube 410 (e.g., length, wall thickness, inner diameter, etc.), and/or combinations thereof. In some examples, the jet orifices 418 may have a cross-sectional dimension in the range of about 0.0018 inches (45.72 micrometers) to about 0.0022 inches (55.88 micrometers). However, the jet orifices 418 can have a cross-sectional dimension of less than 0.0018 inches (45.72 micrometers) or greater than 0.0022 inches (55.88 micrometers), as desired.

Infusion of motive fluid through the lumen 414 of the supply tube wall 412 may result in fluid being jetted through the jet orifices 418 and the generation of a proximally directed aspiration force. At least some of the jet orifices 418*a-c* may be angled in a proximal direction or otherwise designed to infuse fluid (e.g., a motive fluid, a liquid, a gas or air, steam, a fluid with particles disposed therein, or the like) through the jet orifices 418*a-c* and into the lumen 406 of the catheter body 402 in a generally proximal direction as depicted by lines 420*a-c* representing motive jetted fluid projecting generally proximally from the jet orifices 418*a-c*. For example, each of the jet orifices 418*a-c* may be arranged at an acute angle to the longitudinal axis of the supply tube wall 412 such that the jet orifices 418*a-c* angle in a proximal direction. In some embodiments, one or more of the jet orifices 418*d* may be designed to infuse fluid (e.g., a motive fluid, a liquid, a gas or air, steam, a fluid with particles disposed therein, or the like) through the jet orifice(s) 418*d* and into the lumen 406 of the catheter body 402 in a generally distal direction as depicted by lines 420*d* representing motive jetted fluid projecting generally distally from the jet orifice 418*d*. For example, the jet orifice 418*d* may be arranged at an oblique angle to the longitudinal axis of the supply tube wall 412 such that the jet orifice 418*d* angles in a distal direction. It is contemplated that an angle of the jet orifices 418 and thus the motive jetted fluid 420 may be varied to adjust the velocity of the fluid exiting the jet orifices 418. As further described herein, the supply tube wall 412 may include one or more, or a plurality of proximally oriented or directed jet orifices 418*a*, 418*b*, 418*c* (i.e., jet orifices configured to direct fluid infused through the lumen 414 of the supply tube wall 412 in a proximal direction) and the supply tube wall 412 may include one or more, or a plurality of distally oriented or directed jet orifices 418*d* (i.e., jet orifices configured to direct fluid infused through the lumen 414 of the supply tube wall 412 in a distal direction). In some examples, the distally projecting jet orifice 418*d* may be axially aligned with one or more of the proximally projecting jet orifices 418*a-c*. In other examples, the distally projecting jet orifice 418*d* may be circumferentially offset from one or more of the proximally projecting jet orifices 418*a-c*. For example, the distally projecting jet orifice 418*d* may be circumferentially offset from one or more of the proximally projecting jet orifices 418*a-c* by in the range of about 10° to about 350° or about 45° to about 135°.

The distally projecting jet orifice 418*d* may be the distalmost jet orifice, with the proximally projecting jet orifices 418*a-c* positioned proximal of the distally projecting jet orifice 418*d*. However, this is not required. In some embodiments, the distally projecting jet orifice 418*d* may be positioned proximal to at least one proximally projecting jet orifice 418*a-c*. While the supply tube wall 412 is illustrated as including only a single distally projecting jet orifice 418*d*, the supply tube wall 412 may include more than one distally projecting jet orifice, as desired. When more than one distally projecting jet orifice 418*d* is provided, the distally projecting jet orifices may be positioned at differing axial and/or circumferential locations from one another or similar axial and/or circumferential locations as one another, as desired. The distally projecting jet orifice(s) 418*d* may break up particles as they are drawn into the lumen 406 of the catheter body 402 while the proximally projecting jet orifices 418*a-c* may move particles proximally along the catheter body 402.

The performance of the thrombectomy catheter 400 and the high-pressure fluid supply tube 410 may be directly related to the velocity of the motive jetted fluid 420 exiting the jet orifices 418 and the shear-induced turbulent flux created by the jetted motive fluid 420. For example, the more powerful the jetted motive fluid 420, the higher the aspiration rates may be. It is further contemplated that the performance of the jet-powered aspiration catheter 400 may be directly related to the speed at which the clot can be entrained into the catheter 400, macerated, and removed from the body. Any clogging that occurs within the catheter body 402 may reduce or completely stop the removal of the clot. The addition of the distally projecting jet orifice 418*d* may macerate any clot that enters the distal opening 408 of the catheter body 402 thus helping prevent clogging. For example, at the point of impingement of the distally oriented motive jetted fluid 420*d* the motive jetted fluid 420*d* may deflect distally creating flow out the tip of the distal opening 408 of the catheter body 402, effectively macerating any clot that enters the tip of the device, and eliminating or reducing risk of the distal opening 408 of the catheter body 402 becoming blocked or clogged. It is contemplated that the properties (size, shape, angle, number, spacing, etc.) of the jet orifices 418 may be varied to obtain a fluid velocity that creates an optimum de-clogging effect without hindering the proximal flow of a clot within the lumen 406 of the catheter body 402 or the clot evacuation rate.

The distally projecting jet orifice 418*d* may be proximally spaced a distance from the distal opening 408 of the catheter body 402. It is contemplated that the longitudinal location of the distally projecting jet orifice 418*d* on the supply tube wall 412 and relative to the distal opening 408 of the catheter body 402 may be varied based on a size of the aperture of the distally projecting jet orifice 418*d*, the velocity of the fluid within the lumen 414 of the supply tube wall 412, the angle of the distally projecting jet orifice 418*d*, or combinations thereof, etc. to ensure the distally oriented motive jetted fluid 420*d* impinges the inner surface of the catheter body 402. In one illustrative example, the distally projecting jet orifice 418*d* may be positioned such that the distally oriented motive jetted fluid 420*d* impinges an inner surface of the catheter body 402 such that the distally oriented motive jetted fluid 420*d* does not damage the vessel. For example, the distally projecting jet orifice 418*d* may be positioned such that the distally oriented motive jetted fluid 420*d* impinges an inner surface of the catheter body 402 in the range of about 0.070 inches (1.778 millimeters) to about 0.090 inches (2.286 millimeters) proximal to the distal end of the catheter body 402. This is just one example. The impingement location of the motive jetted fluid 420*d* of the distally projecting jet orifice 418*d* may be less than 0.070 inches (1.778 millimeters) or more than 0.090 inches (2.286 millimeters) proximal to the distal end of the catheter body 402, as desired.

In some instances, the jet orifices 418 may be oriented at an angle relative to the longitudinal axis of the supply tube wall 412. For example, the proximally projecting jet orifices 418*a-c* may be oriented at an oblique (e.g., acute) angle relative to the longitudinal axis of the supply tube wall 412 and/or oriented at an angle greater than zero degrees and less than ninety degrees relative to the longitudinal axis of the supply tube wall 412. It is contemplated that a distally projecting jet orifice 418*d* may be oriented at an oblique (e.g., obtuse) angle relative to the longitudinal axis of the supply tube wall 412 and/or oriented at an angle greater than 90 degrees and less than 180 degrees relative to the longitudinal axis of the supply tube wall 412. In other instances, the jet orifices 418 may be oriented perpendicular to the longitudinal axis of the supply tube wall 412 (e.g., at an angle of about 90 degrees relative to the longitudinal axis of the supply tube wall 412). The angle may or may not be the same for all the jet orifices 418.

In at least some instances, the jet orifices 418 may be understood as being arranged in series. In other words, the jet orifices 418 may be arranged such that adjacent jet orifices 418 are spaced longitudinally apart at various locations along the longitudinal axis of the supply tube wall 412. For example, the jet orifices 418 may be uniformly or non-uniformly spaced along of a length of the supply tube wall 412. This may position the jet orifices 418 at axially spaced apart locations within the catheter body 402 and along the length thereof. For example, the jet orifices 418 may be spaced along an entire length of the supply tube wall 412 and correspondingly along an entire length of the catheter body 402, or portions thereof, as desired. In some examples, the jet orifices 418 may be spaced at intervals in the range of every 5 inches (12.7 centimeters (cm)) to every 15 inches (38.1 cm), or in the range of every 6 inches (15.2 cm) to every 12 inches (30.5 cm) along a length of the supply tube wall 412. In other instances, the spacing between the jet orifices 418 may be less than every 5 inches (12.7 cm) or greater than every 15 inches (38.1 cm). Accordingly, motive fluid leaves via the jet orifices 418 forming a jetted motive fluid 420*a-d* (collectively, 420). In some instances, the jetted motive fluid 420 may reach speeds of 17,150 centimeters/second or greater (e.g., half the speed of sound, or greater). This jetted motive fluid 420 enters an entrainment material where the shear layer between the two causes turbulence, mixing, and transfer of momentum. Entrainment material may enter the distal opening 408 and then may be urged proximally by momentum transfer. As the mixture of jetted motive fluid 420 and entrainment material migrates proximally, the material may sequentially approach a number of jet orifices 418. Upon interaction with the jetted motive fluid 420 from each individual jet orifice 418, the momentum in the entrainment material mixture may increase, and the thrombogenic material may more readily flow proximally through the catheter body 402 for removal. The increase in momentum may allow for the catheter body 402 to be used without a second or outflow orifice (e.g., positioned proximally of the distal opening 408). Alternatively, some of the entrapped thrombogenic material may exit the catheter body 402 through a second orifice (not shown), e.g., in a sidewall of the catheter body 402, positioned proximal to the distal opening 408, recirculate to the distal opening 408 (e.g., one or more times), and then move proximally through the lumen 406 of the catheter body 402.

It is further contemplated that the distally oriented motive jetted fluid 420*d* may be partially to fully entrained by the force generated by the proximally oriented motive jetted fluid 420*a-c*. When the clot/thrombus reaches the distally oriented motive jetted fluid 420*d*, the shear stress may masticate the clot/thrombus. It is contemplated that when the distal opening 408 of the catheter body 402 is sealed with a clot/thrombus, the force generated by the proximally oriented motive jetted fluid 420*a-c* may be transferred to the surface of the clot/thrombus in a proximal direction. As a result, the distally oriented motive jetted fluid 420*d* may no longer be entrained and may transfer force in the distal direction to the surface of the clot/thrombus. Thus, when the distal opening 408 is clogged or plugged, an extreme shear mechanism of action is created where the distal and proximal force vectors combine together to focus all of the shear stress to the surface of the clot/thrombus to masticate the clot/thrombus and unplug the distal opening 408. It is contemplated that the shear stress on the clot/thrombus may be much larger in magnitude when the distally oriented motive jetted fluid 420*d* is at a smaller angle (e.g., closer to 180 degrees relative to the longitudinal axis of the supply tube wall 412 than to orthogonal to the longitudinal axis of the supply tube wall 412).

Figure 5:
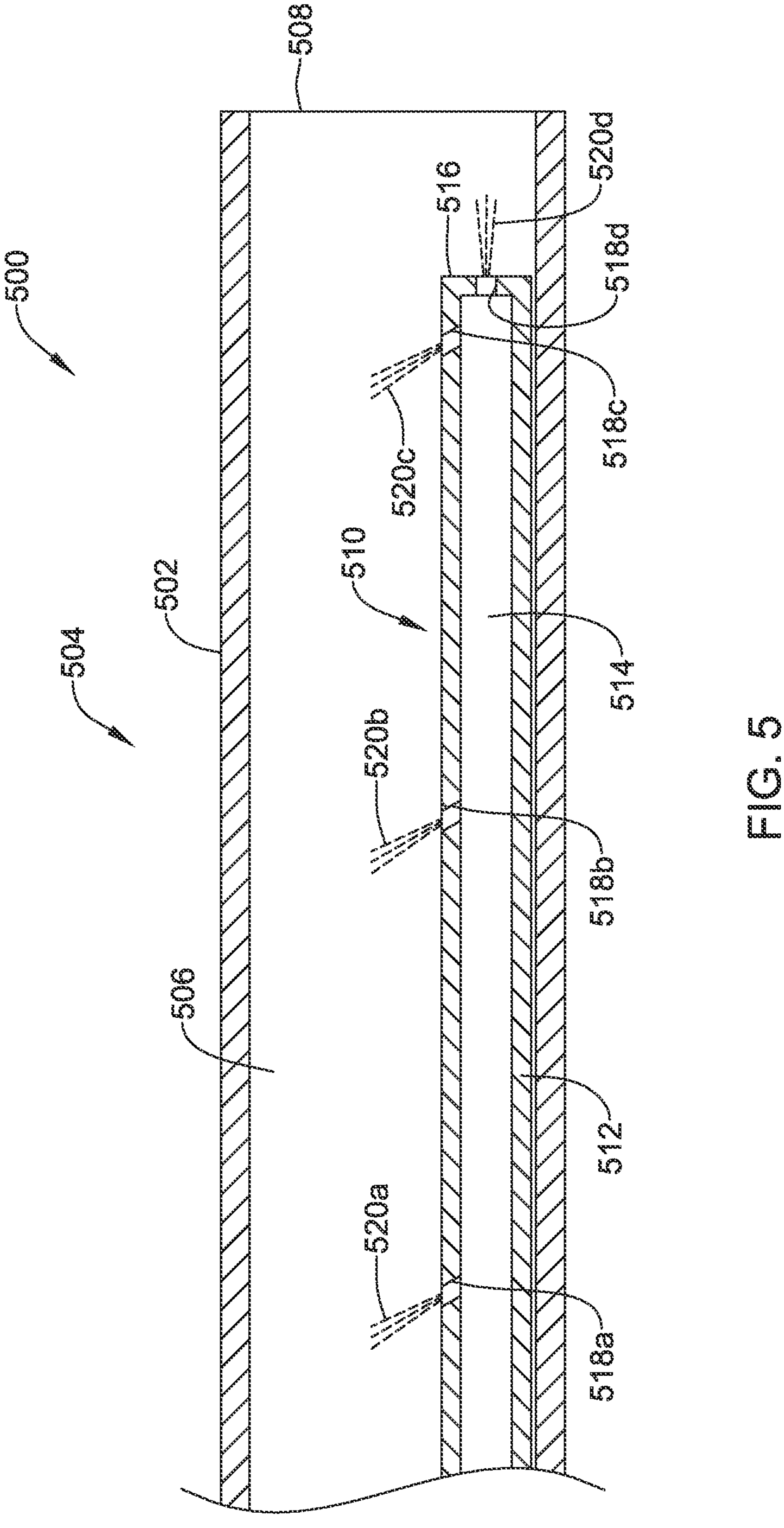
FIG. 5 is a longitudinal cross-sectional view of a distal end region of another illustrative thrombectomy catheter.

FIG. 5 is a cross-sectional view of a distal end region 504 of another illustrative thrombectomy catheter 500. The thrombectomy catheter 500 may be one illustrative example of the thrombectomy catheter 58 described above. The thrombectomy catheter 500 may include a tubular member or catheter body 502 extending from a proximal end region (not explicitly shown) configured to remain outside the body to a distal end region 504. The catheter body 502 may be one illustrative example of, or be in fluid communication with, the effluent return tube 66 of the thrombectomy catheter 58 described above. A lumen 506 may extend from the proximal end region to the distal end region 504 of the catheter body 502. The catheter body 502 may terminate at a distally facing distal opening 508 at the distal end of the catheter body 502. In some instances, the distal opening 508 may be in a plane that extends generally orthogonal to a longitudinal axis of the catheter body 502. In other instances, the distal opening 508 may be in a plane that extends generally oblique to a longitudinal axis of the catheter body 502. Generally, the distal opening 508 may be an entrainment inflow orifice. While not explicitly shown, the catheter body 502 may include one or more markers (e.g., radiopaque marker bands) disposed along the catheter body 502. Further, while not explicitly shown, in some embodiments, the catheter body 502 may include one or more openings extending through a sidewall thereof, if desired.

The thrombectomy catheter 500 may further include a high-pressure fluid supply tube 510. The high-pressure fluid supply tube 510 may be one illustrative example of, or be in fluid communication with, the high-pressure fluid supply tube 66 of the thrombectomy catheter 58 described above. The high-pressure fluid supply tube 510 may be disposed within and extend through the lumen 506 of the catheter body 502. The high-pressure fluid supply tube 510 may include a supply tube wall 512 defining a lumen or fluid pathway 514 extending therethrough. In at least some instances, the high-pressure fluid supply tube 510 may have a partially closed distal end 516. The high-pressure fluid supply tube 510 may extend along a length of the catheter body 502 with the distal end 516 located within the lumen 506 of the catheter body 502 proximal to the distal opening 508 at the distal end of the catheter body 502. A proximal end of the high-pressure fluid supply tube 510 may be in fluid communication with the pump 56 described herein, to provide high-pressure fluid to the fluid pathway 514 of the high-pressure fluid supply tube 510.

A plurality of jet orifices 518*a-d* (collectively, 518) may be defined along the supply tube wall 512. For example, the supply tube wall 512 may include two, three, four, five, six, or more jet orifices 518. The jet orifices 518 may be spaced along the supply tube wall 512 at any desired intervals. For example, each of the jet orifices 518 may be equidistantly spaced from adjacent jet orifices 518 along the length of the supply tube wall 512. In other instances, the jet orifices 518 may be arranged such that the spacing between adjacent jet orifices 518 near the distal end of the supply tube wall 512 is closer than the spacing between adjacent jet orifices 518 near the proximal end of the supply tube wall 512. For instance, the spacing between the orifices 518 may gradually increase as you move proximally along the length of the shaft, or the spacing may increase in a step-wise configuration. In some instances, some or all of the jet orifices 518 may be axially aligned along the supply tube wall 512. In other instances, one or more of the jet orifices 518 may be circumferentially offset from one another about the supply tube wall 512. A number of patterns are contemplated including a helical pattern, a pattern where no two jet orifices 518 are disposed at the same axial location, a regular pattern including two or more jet orifices 518 disposed at the same axial location, an irregular pattern (where some of the jet orifices 518 may or may not be disposed at the same axial location), etc. The jet orifices 518 may be formed using a suitable method such as electron discharge machining, etching, cutting (e.g., including laser cutting), or the like. In some instances, one or more of the jet orifices 518 may have a substantially round shape. In other instances, one or more of the jet orifices 518 may have a substantially non-round shape (e.g., oval, polygonal, irregular, etc.). In some instances, the jet orifices 518 may be beveled or otherwise include a beveled surface. It is contemplated that a size and/or a shape of the jet orifices 518 may be varied to vary the velocity of the fluid exiting the jet orifices. For example, decreasing the size of the jet orifices 518 may increase the velocity of the fluid exiting the jet orifices 518. In some embodiments, the size of the jet orifices 518 may be varied based on the pressure capacity of the thrombectomy system, the number of jet orifices, the dimensions of the high-pressure fluid supply tube 510 (e.g., length, wall thickness, inner diameter, etc.), and/or combinations thereof. In some examples, the jet orifices 518 may have a cross-sectional dimension in the range of about 0.0018 inches (45.72 micrometers) to about 0.0022 inches (55.88 micrometers). However, the jet orifices 518 can have a cross-sectional dimension of less than 0.0018 inches (45.72 micrometers) or greater than 0.0022 inches (55.88 micrometers), as desired.

Infusion of motive fluid through the lumen 514 of the supply tube wall 512 may result in fluid being jetted through the jet orifices 518 and the generation of a proximally directed aspiration force. At least some of the jet orifices 518*a*-*c* may extend through a circumferential sidewall of the supply tube wall 512. It is contemplated that at least some of the jet orifices 518*a*-*c* may be angled in a proximal direction or otherwise designed to infuse fluid (e.g., a motive fluid, a liquid, a gas or air, steam, a fluid with particles disposed therein, or the like) through the jet orifices 518*a*-*c* and into the lumen 506 of the catheter body 502 in a generally proximal direction as depicted by lines 520*a*-*c* representing motive jetted fluid projecting generally proximally from the jet orifices 518*a*-*c*. For example, each of the jet orifices 518*a*-*c* may be arranged at an acute angle to the longitudinal axis of the supply tube wall 512 such that the jet orifices 518*a*-*c* angle in a proximal direction. In some embodiments, one or more of the jet orifices 518*d* may be designed to infuse fluid (e.g., a motive fluid, a liquid, a gas or air, steam, a fluid with particles disposed therein, or the like) through the jet orifice(s) 518*d* and into the lumen 506 of the catheter body 502 in a generally distal direction as depicted by lines 520*d* representing motive jetted fluid projecting generally distally from the jet orifice 518*d*. For example, the jet orifice 518*d* may be arranged in line with the longitudinal axis of the supply tube wall 512 such that the jet orifice 518*d* expels fluid distally in a direction generally parallel to the longitudinal axis of the supply tube wall 512.

As further described herein, the supply tube wall 512 may include one or more, or a plurality of proximally oriented or directed jet orifices 518*a*, 518*b*, 518*c* (i.e., jet orifices configured to direct fluid infused through the lumen 514 of the supply tube wall 512 in a proximal direction) and the supply tube wall 512 may include one or more, or a plurality of distally oriented or directed jet orifices 518*d* (i.e., jet orifices configured to direct fluid infused through the lumen 514 of the supply tube wall 512 in a distal direction).

It is contemplated that the jet orifice 518*d* may be formed though the distal end 516 of the supply tube wall 512. The distally projecting jet orifice 518*d* may have diameter that is less than an inner diameter of the lumen 514 of the supply tube wall 512. In other examples, a diameter of the distally projecting jet orifice 518*d* may be approximately the same as an inner diameter of the lumen 514 of the supply tube wall 512. In yet other examples, the circumferential sidewalls of the supply tube wall 512 may be beveled at the distal end 516 such that a diameter of the distally projecting jet orifice 518*d* may be greater than a diameter of the lumen 514 of the supply tube wall 512. It is contemplated that the distal end 516 of the supply tube wall 512 may be proximal to the distal opening 508 of the catheter body 502 to fully entrain the distally projecting jet orifice 518*d*.

The distally projecting jet orifice 518*d* may be the distalmost jet orifice, with the proximally projecting jet orifices 518*a*-*c* positioned proximal of the distally projecting jet orifice 518*d*. While the supply tube wall 512 is illustrated as including only a single distally projecting jet orifice 518*d*, the supply tube wall 512 may include more than one distally projecting jet orifice, as desired. In some cases, more than one distally projecting jet orifices 418*d* may be formed in the distal end 516 of the supply tube wall 512. Alternatively, or additionally, one or more additional distally projecting jet orifices 518*d* may be formed in a circumferential sidewall of the supply tube wall 512. When more than one distally projecting jet orifice 518*d* is provided, one or more distally projecting jet orifices may extend through a circumferential sidewall of the supply tube wall 512 at differing axial and/or circumferential locations from one another or similar axial and/or circumferential locations as one another, as desired. The distally projecting jet orifice(s) 518*d* may break up particles as they are drawn into the lumen 506 of the catheter body 502 while the proximally projecting jet orifices 518*a*-*c* may move particles proximally along the catheter body 502.

The performance of the thrombectomy catheter 500 and the high-pressure fluid supply tube 510 may be directly related to the velocity of the motive jetted fluid 520 exiting the jet orifices 518 and the shear-induced turbulent flux created by the jetted motive fluid 520. For example, the more powerful the jetted motive fluid 520, the higher the aspiration rates may be. It is further contemplated that the performance of the jet-powered aspiration catheter 500 may be directly related to the speed at which the clot can be entrained into the catheter 500, macerated, and removed from the body. Any clogging that occurs within the catheter body 502 may reduce or completely stop the removal of the clot. The addition of the distally projecting jet orifice 518*d* may macerate any clot that enters the distal opening 508 of the catheter body 502 thus helping prevent clogging. For example, at the point of impingement of the distally oriented motive jetted fluid 520*d* the motive jetted fluid 520*d* may deflect distally creating flow out the tip of the distal opening 508 of the catheter body 502, effectively macerating any clot that enters the distal opening 508 of the catheter body 502, and eliminating or reducing risk of the distal opening 508 of the catheter body 502 becoming blocked or clogged. It is contemplated that the properties (size, shape, angle, number, spacing, etc.) of the jet orifices 518 may be varied to obtain a fluid velocity that creates an optimum de-clogging effect without hindering the proximal flow of a clot within the lumen 506 of the catheter body 502 or the clot evacuation rate.

The distally projecting jet orifice 518*d* may be proximally spaced a distance from the distal opening 508 of the catheter body 502. It is contemplated that the longitudinal location of the distally projecting jet orifice 518*d* on the supply tube wall 512 and relative to the distal opening 508 of the catheter body 502 may be varied based on a size of the aperture of the distally projecting jet orifice 518*d*, the velocity of the fluid within the lumen 514 of the supply tube wall 512, the angle of the distally projecting jet orifice 518*d*, or combinations thereof, etc. to ensure the distally oriented motive jetted fluid 520*d* does not impinge the vessel wall.

In some instances, the jet orifices 518 may be oriented at an angle relative to the longitudinal axis of the supply tube wall 512. For example, the proximally projecting jet orifices 518*a-c* may be oriented at an oblique (e.g., acute) angle relative to the longitudinal axis of the supply tube wall 512 and/or oriented at an angle greater than zero degrees and less than ninety degrees relative to the longitudinal axis of the supply tube wall 512. It is contemplated that a distally projecting jet orifice 518*d* may be oriented along or parallel to the longitudinal axis of the supply tube wall 512. In other instances, the jet orifices 518 may be oriented perpendicular to the longitudinal axis of the supply tube wall 512 (e.g., at an angle of about 90 degrees relative to the longitudinal axis of the supply tube wall 512). The angle may or may not be the same for all the jet orifices 518. It is contemplated that an angle of the jet orifices 518 and thus the motive jetted fluid 520 may be varied by to adjust the velocity of the fluid exiting the jet orifices 518.

In at least some instances, the jet orifices 518 may be understood as being arranged in series. In other words, the jet orifices 518 may be arranged such that adjacent jet orifices 518 are spaced longitudinally apart at various locations along the longitudinal axis of the supply tube wall 512. For example, the jet orifices 518 may be uniformly or non-uniformly spaced along of a length of the supply tube wall 512. This may position the jet orifices 518 at axially spaced apart locations within the catheter body 502 and along the length thereof. For example, the jet orifices 518 may be spaced along an entire length of the supply tube wall 512 and correspondingly along an entire length of the catheter body 502, or portions thereof, as desired. In some examples, the jet orifices 518 may be spaced at intervals in the range of every 5 inches (12.7 centimeters (cm)) to every 15 inches (38.1 cm), or in the range of every 6 inches (15.2 cm) to every 12 inches (30.5 cm) along a length of the supply tube wall 512. In other instances, the spacing between the jet orifices 518 may be less than every 5 inches (12.7 cm) or greater than every 15 inches (38.1 cm). Accordingly, motive fluid leaves via the jet orifices 518 forming a jetted motive fluid 520*a-d* (collectively, 520). In some instances, the jetted motive fluid 520 may reach speeds of 17,150 centimeters/second or greater (e.g., half the speed of sound, or greater). This jetted motive fluid 520 enters an entrainment material where the shear layer between the two causes turbulence, mixing, and transfer of momentum. Entrainment material may enter the distal opening 508 and then may be urged proximally by momentum transfer. As the mixture of jetted motive fluid 520 and entrainment material migrates proximally, the material may sequentially approach a number of jet orifices 518. Upon interaction with the jetted motive fluid 520 from each individual jet orifice 518, the momentum in the entrainment material mixture may increase, and the thrombogenic material may more readily flow proximally through the catheter body 502 for removal. The increase in momentum may allow for the catheter body 502 to be used without a second or outflow orifice (e.g., positioned proximally of the distal opening 508). Alternatively, some of the entrapped thrombogenic material may exit the catheter body 502 through a second orifice (not shown), e.g., in a sidewall of the catheter body 502, positioned proximal to the distal opening 508, recirculate to the distal opening 508 (e.g., one or more times), and then move proximally through the lumen 506 of the catheter body 502.

It is further contemplated that the distally oriented motive jetted fluid 520*d* may be partially to fully entrained by the force generated by the proximally oriented motive jetted fluid 520*a-c*. When the clot/thrombus reaches the distally oriented motive jetted fluid 520*d*, the shear stress may masticate the clot/thrombus. It is contemplated that when the distal opening 508 of the catheter body 502 is sealed with a clot/thrombus, the force generated by the proximally oriented motive jetted fluid 520*a-c* may be transferred to the surface of the clot/thrombus in a proximal direction. As a result, the distally oriented motive jetted fluid 520*d* may no longer be entrained and may transfer force in the distal direction to the surface of the clot/thrombus. Thus, when the distal opening 508 is clogged or plugged, an extreme shear mechanism of action is created where the distal and proximal force vectors combine together to focus all of the shear stress to the surface of the clot/thrombus to masticate the clot/thrombus and unplug the distal opening 508.

Figure 6:
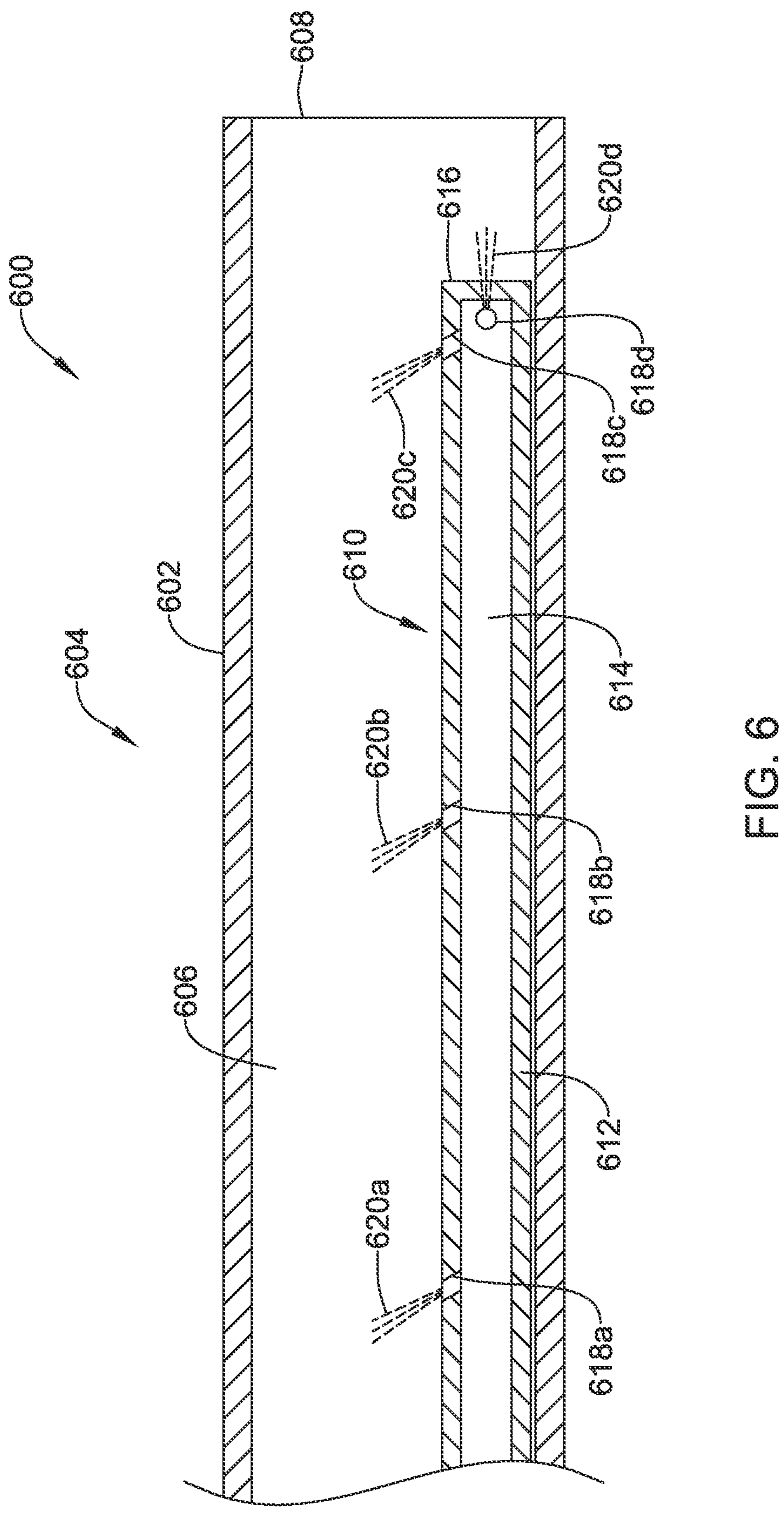
FIG. 6 is a longitudinal cross-sectional view of a distal end region of another illustrative thrombectomy catheter.

FIG. 6 is a cross-sectional view of a distal end region 604 of another illustrative thrombectomy catheter 600. The thrombectomy catheter 600 may be one illustrative example of the thrombectomy catheter 58 described above. The thrombectomy catheter 600 may include a tubular member or catheter body 602 extending from a proximal end region (not explicitly shown) configured to remain outside the body to a distal end region 604. The catheter body 602 may be one illustrative example of, or be in fluid communication with, the effluent return tube 66 of the thrombectomy catheter 58 described above. A lumen 606 may extend from the proximal end region to the distal end region 604 of the catheter body 602. The catheter body 602 may terminate at a distally facing distal opening 608 at the distal end of the catheter body 602. In some instances, the distal opening 608 may be in a plane that extends generally orthogonal to a longitudinal axis of the catheter body 602. In other instances, the distal opening 608 may be in a plane that extends generally oblique to a longitudinal axis of the catheter body 602. Generally, the distal opening 608 may be an entrainment inflow orifice. While not explicitly shown, the catheter body 602 may include one or more markers (e.g., radiopaque marker bands) disposed along the catheter body 602. Further, while not explicitly shown, in some embodiments, the catheter body 602 may include one or more openings extending through a sidewall thereof, if desired.

The thrombectomy catheter 600 may further include a high-pressure fluid supply tube 610. The high-pressure fluid supply tube 610 may be one illustrative example of, or be in fluid communication with, the high-pressure fluid supply tube 66 of the thrombectomy catheter 58 described above. The high-pressure fluid supply tube 610 may be disposed within and extend through the lumen 606 of the catheter body 602. The high-pressure fluid supply tube 610 may include a supply tube wall 612 defining a lumen or fluid pathway 614 extending therethrough. In at least some instances, the high-pressure fluid supply tube 610 may have a closed distal end 616. Because of this, fluid may be able to pass through the fluid pathway 614 but does not exit the distal end. The high-pressure fluid supply tube 610 may extend along a length of the catheter body 602 with the distal end 616 located within the lumen 606 of the catheter body 602 proximal to the distal opening 608 at the distal end of the catheter body 602. A proximal end of the high-pressure fluid supply tube 610 may be in fluid communication with the pump 56 described herein, to provide high-pressure fluid to the fluid pathway 614 of the high-pressure fluid supply tube 610.

A plurality of jet orifices 618*a-d* (collectively, 618) may be defined along the supply tube wall 612. For example, the supply tube wall 612 may include two, three, four, five, six, or more jet orifices 618. The jet orifices 618 may be spaced along the supply tube wall 612 at any desired intervals. For example, each of the jet orifices 618 may be equidistantly spaced from adjacent jet orifices 618 along the length of the supply tube wall 612. In other instances, the jet orifices 618 may be arranged such that the spacing between adjacent jet orifices 618 near the distal end of the supply tube wall 612 is closer than the spacing between adjacent jet orifices 618 near the proximal end of the supply tube wall 612. For instance, the spacing between the orifices 618 may gradually increase as you move proximally along the length of the shaft, or the spacing may increase in a step-wise configuration. In some instances, some or all of the jet orifices 618 may be axially aligned along the supply tube wall 612. In other instances, one or more of the jet orifices 618 may be circumferentially offset from one another about the supply tube wall 612. A number of patterns are contemplated including a helical pattern, a pattern where no two jet orifices 618 are disposed at the same axial location, a regular pattern including two or more jet orifices 618 disposed at the same axial location, an irregular pattern (where some of the jet orifices 618 may or may not be disposed at the same axial location), etc. The jet orifices 618 may be formed using a suitable method such as electron discharge machining, etching, cutting (e.g., including laser cutting), or the like. In some instances, one or more of the jet orifices 618 may have a substantially round shape. In other instances, one or more of the jet orifices 618 may have a substantially non-round shape (e.g., oval, polygonal, irregular, etc.). In some instances, the jet orifices 618 may be beveled or otherwise include a beveled surface. It is contemplated that a size and/or a shape of the jet orifices 618 may be varied to vary the velocity of the fluid exiting the jet orifices. For example, decreasing the size of the jet orifices 618 may increase the velocity of the fluid exiting the jet orifices 618. In some embodiments, the size of the jet orifices 618 may be varied based on the pressure capacity of the thrombectomy system, the number of jet orifices, the dimensions of the high-pressure fluid supply tube 610 (e.g., length, wall thickness, inner diameter, etc.), and/or combinations thereof. In some examples, the jet orifices 618 may have a cross-sectional dimension in the range of about 0.0018 inches (45.72 micrometers) to about 0.0022 inches (55.88 micrometers). However, the jet orifices 608 can have a cross-sectional dimension of less than 0.0018 inches (45.72 micrometers) or greater than 0.0022 inches (55.88 micrometers), as desired.

Infusion of motive fluid through the lumen 614 of the supply tube wall 612 may result in fluid being jetted through the jet orifices 618 and the generation of a proximally directed aspiration force. At least some of the jet orifices 618*a-c* may extend through a circumferential sidewall of the supply tube wall 612. It is contemplated that at least some of the jet orifices 618*a-c* may be angled in a proximal direction or otherwise designed to infuse fluid (e.g., a motive fluid, a liquid, a gas or air, steam, a fluid with particles disposed therein, or the like) through the jet orifices 618*a-c* and into the lumen 606 of the catheter body 602 in a generally proximal direction as depicted by lines 620*a-c* representing motive jetted fluid projecting generally proximally from the jet orifices 618*a-c*. For example, each of the jet orifices 618*a-c* may be arranged at an acute angle to the longitudinal axis of the supply tube wall 612 such that the jet orifices 618*a-c* angle in a proximal direction. In some embodiments, one or more of the jet orifices 618*d* may be designed to infuse fluid (e.g., a motive fluid, a liquid, a gas or air, steam, a fluid with particles disposed therein, or the like) through the jet orifice(s) 618*d* and into the lumen 606 of the catheter body 602 in a generally distal direction as depicted by lines 620*d* representing motive jetted fluid projecting generally distally from the jet orifice 618*d*. For example, the jet orifice 618*d* may be arranged at an oblique angle to the longitudinal axis of the supply tube wall 612 such that the jet orifice 618*d* angles in a distal direction.

As further described herein, the supply tube wall 612 may include one or more, or a plurality of proximally oriented or directed jet orifices 618*a*, 618*b*, 618*c* (i.e., jet orifices configured to direct fluid infused through the lumen 614 of the supply tube wall 612 in a proximal direction) and the supply tube wall 612 may include one or more, or a plurality of distally oriented or directed jet orifices 618*d* (i.e., jet orifices configured to direct fluid infused through the lumen 614 of the supply tube wall 612 in a distal direction).

In some embodiments, the distally projecting jet orifice 618*d* may be circumferentially offset from the proximally projecting jet orifices 618*a-d*. In the illustrated embodiment, the distally projecting jet orifice 618*d* may be spaced in the range of about 45° to about 135° or approximately 90° about the circumference of the supply tube wall 612 from the proximally projecting jet orifices 618*a-c*. However, other circumferential spacing intervals may be used, as desired. For example, the distally projecting jet orifice 618*d* may be spaced in the range of about 10° to about 350°, about 45° to about 135°, or about 60° to about 120° from the proximally projecting jet orifices 618*a-d*. However, it is contemplated that the distally projecting jet orifice 618*d* may not be positioned adjacent the catheter body 602. It is contemplated that positioning the distally projecting jet orifice 618*d* circumferentially offset from the proximal projecting jet orifices 618*a-c* may create a spiral effect with motive jetted fluid 620 thus increasing mastication of the clots or debris.

The distally projecting jet orifice 618*d* may be the distalmost jet orifice, with the proximally projecting jet orifices 618*a-c* positioned proximal of the distally projecting jet orifice 618*d*. However, this is not required. In some embodiments, the distally projecting jet orifice 618*d* may be positioned proximal to at least one proximally projecting jet orifice 618*a-c*. While the supply tube wall 612 is illustrated as including only a single distally projecting jet orifice 618*d*, the supply tube wall 612 may include more than one distally projecting jet orifice, as desired. When more than one distally projecting jet orifice 618*d* is provided, the distally projecting jet orifices may be positioned at differing axial and/or circumferential locations from one another or similar axial and/or circumferential locations as one another, as desired. The distally projecting jet orifice(s) 618*d* may break up particles as they are drawn into the lumen 606 of the catheter body 602 while the proximally projecting jet orifices 618*a-c* may move particles proximally along the catheter body 602.

The performance of the thrombectomy catheter 600 and the high-pressure fluid supply tube 610 may be directly related to the velocity of the motive jetted fluid 620 exiting the jet orifices 618 and the shear-induced turbulent flux created by the jetted motive fluid 620. For example, the more powerful the jetted motive fluid 620, the higher the aspiration rates may be. It is further contemplated that the performance of the jet-powered aspiration catheter 600 may be directly related to the speed at which the clot can be entrained into the catheter 600, macerated, and removed from the body. Any clogging that occurs within the catheter body 602 may reduce or completely stop the removal of the clot. The addition of the distally projecting jet orifice 618*d* may macerate any clot that enters the distal opening 608 of the catheter body 602 thus helping prevent clogging. For example, at the point of impingement of the distally oriented motive jetted fluid 620*d* the motive jetted fluid 620*d* may deflect distally creating flow out the tip of the distal opening 608 of the catheter body 602, effectively macerating any clot that enters the distal opening 608 of the catheter body 602, and eliminating or reducing risk of the distal opening 608 of the catheter body 602 becoming blocked or clogged. It is contemplated that the properties (size, shape, angle, number, spacing, etc.) of the jet orifices 618 may be varied to obtain a fluid velocity that creates an optimum de-clogging effect without hindering the proximal flow of a clot within the lumen 606 of the catheter body 602 or the clot evacuation rate.

The distally projecting jet orifice 618*d* may be proximally spaced a distance from the distal opening 608 of the catheter body 602. It is contemplated that the longitudinal location of the distally projecting jet orifice 618*d* on the supply tube wall 612 and relative to the distal opening 608 of the catheter body 602 may be varied based on a size of the aperture of the distally projecting jet orifice 618*d*, the velocity of the fluid within the lumen 614 of the supply tube wall 612, the angle of the distally projecting jet orifice 618*d*, or combinations thereof, etc. to ensure the distally oriented motive jetted fluid 620*d* impinges the inner surface of the catheter body 602. In one illustrative example, the distally projecting jet orifice 618*d* may be positioned such that the distally oriented motive jetted fluid 620*d* impinges an inner surface of the catheter body 602 such that the distally oriented motive jetted fluid 620*d* does not damage the vessel. For example, the distally projecting jet orifice 618*d* may be positioned such that the distally oriented motive jetted fluid 620*d* impinges an inner surface of the catheter body 602 in the range of about 0.070 inches (1.778 millimeters) to about 0.090 inches (2.286 millimeters) proximal to the distal end of the catheter body 602. This is just one example. The impingement location of the motive jetted fluid 620*d* of the distally projecting jet orifice 418*d* may be less than 0.070 inches (1.778 millimeters) or more than 0.090 inches (2.286 millimeters) proximal to the distal end of the catheter body 602, as desired.

In some instances, the jet orifices 618 may be oriented at an angle relative to the longitudinal axis of the supply tube wall 612. For example, the sidewalls of the proximally projecting jet orifices 618*a-c* may be oriented at an oblique (e.g., acute) angle relative to the longitudinal axis of the supply tube wall 612 and/or oriented at an angle greater than zero degrees and less than ninety degrees relative to the longitudinal axis of the supply tube wall 612. It is contemplated that the sidewalls of a distally projecting jet orifice 618*d* may be oriented at an oblique (e.g., obtuse) angle relative to the longitudinal axis of the supply tube wall 612 and/or oriented at an angle greater than 90 degrees and less than 180 degrees relative to the longitudinal axis of the supply tube wall 612. In other instances, the jet orifices 618 may be oriented perpendicular to the longitudinal axis of the supply tube wall 612 (e.g., at an angle of about 90 degrees relative to the longitudinal axis of the supply tube wall 612). The angle may or may not be the same for all the jet orifices 618. It is contemplated that an angle of the jet orifices 618 and thus the motive jetted fluid 620 may be varied by to adjust the velocity of the fluid exiting the jet orifices 618.

In at least some instances, at least some of the jet orifices 618 may be understood as being arranged in series. In other words, the jet orifices 618 may be arranged such that adjacent jet orifices 618 are spaced longitudinally apart at various locations along the longitudinal axis of the supply tube wall 612. For example, the jet orifices 618 may be uniformly or non-uniformly spaced along of a length of the supply tube wall 612. This may position the jet orifices 618 at axially spaced apart locations within the catheter body 602 and along the length thereof. For example, the jet orifices 618 may be spaced along an entire length of the supply tube wall 612 and correspondingly along an entire length of the catheter body 602, or portions thereof, as desired. In some examples, the jet orifices 618 may be spaced at intervals in the range of every 5 inches (12.7 centimeters (cm)) to every 15 inches (38.1 cm), or in the range of every 6 inches (15.2 cm) to every 12 inches (30.5 cm) along a length of the supply tube wall 612. In other instances, the spacing between the jet orifices 618 may be less than every 5 inches (12.7 cm) or greater than every 15 inches (38.1 cm). Accordingly, motive fluid leaves via the jet orifices 618 forming a jetted motive fluid 620*a-d* (collectively, 620). In some instances, the jetted motive fluid 620 may reach speeds of 17,150 centimeters/second or greater (e.g., half the speed of sound, or greater). This jetted motive fluid 620 enters an entrainment material where the shear layer between the two causes turbulence, mixing, and transfer of momentum. Entrainment material may enter the distal opening 608 and then may be urged proximally by momentum transfer. As the mixture of jetted motive fluid 620 and entrainment material migrates proximally, the material may sequentially approach a number of jet orifices 618. Upon interaction with the jetted motive fluid 620 from each individual jet orifice 618, the momentum in the entrainment material mixture may increase, and the thrombogenic material may more readily flow proximally through the catheter body 602 for removal. The increase in momentum may allow for the catheter body 602 to be used without a second or outflow orifice (e.g., positioned proximally of the distal opening 608). Alternatively, some of the entrapped thrombogenic material may exit the catheter body 602 through a second orifice (not shown), e.g., in a sidewall of the catheter body 602, positioned proximal to the distal opening 608, recirculate to the distal opening 608 (e.g., one or more times), and then move proximally through the lumen 606 of the catheter body 602.

It is further contemplated that the distally oriented motive jetted fluid 620*d* may be partially to fully entrained by the force generated by the proximally oriented motive jetted fluid 620*a-c*. When the clot/thrombus reaches the distally oriented motive jetted fluid 620*d*, the shear stress may masticate the clot/thrombus. It is contemplated that when the distal opening 608 of the catheter body 602 is sealed with a clot/thrombus, the force generated by the proximally oriented motive jetted fluid 620*a-c* may be transferred to the surface of the clot/thrombus in a proximal direction. As a result, the distally oriented motive jetted fluid 620*d* may no longer be entrained and may transfer force in the distal direction to the surface of the clot/thrombus. Thus, when the distal opening 608 is clogged or plugged, an extreme shear mechanism of action is created where the distal and proximal force vectors combine together to focus all of the shear stress to the surface of the clot/thrombus to masticate the clot/thrombus and unplug the distal opening 608.

The materials that can be used for the various components of the thrombectomy catheter, pump/catheter assembly, and/or other devices disclosed herein may include those commonly associated with medical devices. For simplicity purposes, the following discussion makes reference to the pump/catheter assembly and its related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed herein), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the pump/catheter assembly and its related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the pump/catheter assembly and its related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the pump/catheter assembly and its related components to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A thrombectomy catheter, comprising:

a catheter body extending from a proximal end region to a distal end region and including a catheter lumen extending between the proximal end region and the distal end region;

a high-pressure fluid supply tube extending through the catheter lumen from the catheter body proximal end region toward the catheter body distal end region, the high-pressure fluid supply tube configured for communication with a fluid source near the catheter body proximal end region;

at least one proximally projecting jet orifice for expelling at least one proximally oriented fluid jet from said high-pressure fluid supply tube within the catheter lumen in a generally proximal direction, wherein the at least one proximally projecting jet orifice comprises a plurality of proximally projecting jet orifices longitudinally spaced apart from each other along a longitudinal axis of the high-pressure fluid supply tube;

at least one distally projecting jet orifice for expelling at least one distally oriented fluid jet from said high-pressure fluid supply tube within the catheter lumen at an obtuse angle to the longitudinal axis in a generally distal direction; and an entrainment inflow orifice positioned along the catheter body distal end region.

2. The thrombectomy catheter of claim 1, wherein the at least one distally projecting jet orifice is distal to the at least one proximally projecting jet orifice.

3. The thrombectomy catheter of claim 1, wherein the at least one distally oriented fluid jet impinges an inner surface of the catheter body.

4. The thrombectomy catheter of claim 1, wherein the at least one distally projecting jet orifice is axially aligned with the at least one proximally projecting jet orifice.

5. The thrombectomy catheter of claim 1, wherein the at least one distally projecting jet orifice is circumferentially offset from the at least one proximally projecting jet orifice.

6. The thrombectomy catheter of claim 5, wherein the at least one distally projecting jet orifice is circumferentially offset from the at least one proximally projecting jet orifice by in the range of about 45° to about 135°.

7. The thrombectomy catheter of claim 1, wherein a sidewall of the at least one distally projecting jet orifice extends at an obtuse angle relative to the longitudinal axis of the high-pressure fluid supply tube.

8. The thrombectomy catheter of claim 1, wherein a sidewall of the at least one proximally projecting jet orifice extends at an acute angle relative to the longitudinal axis of the high-pressure fluid supply tube.

9. The thrombectomy catheter of claim 1, wherein the at least one distally projecting jet orifice comprises two or more distally projecting jet orifices.

10. The thrombectomy catheter of claim 1, wherein the at least one distally projecting jet orifice extends through a circumferential sidewall of the high-pressure fluid supply tube.

11. A thrombectomy catheter, comprising:

a catheter body extending from a proximal end region to a distal end region and including a catheter lumen extending between the proximal end region and the distal end region;

a high-pressure fluid supply tube extending through the catheter lumen from the catheter body proximal end region toward the catheter body distal end region, the high-pressure fluid supply tube configured for communication with a fluid source near the catheter body proximal end region;

at least one proximally projecting jet orifice for expelling at least one proximally oriented fluid jet from said high-pressure fluid supply tube within the catheter lumen in a generally proximal direction;

at least one distally projecting jet orifice extending through a circumferential sidewall of the high-pressure fluid supply tube, the at least one distally projecting jet orifice for expelling at least one distally oriented fluid jet from said high-pressure fluid supply tube within the catheter lumen in a generally distal direction; and an entrainment inflow orifice positioned along the catheter body distal end region distal of a distal end of the high-pressure fluid supply tube;

wherein the at least one distally oriented fluid jet is configured to impinge an inner surface of the catheter body.

12. The thrombectomy catheter of claim 11, wherein the at least one distally projecting jet orifice is axially aligned with the at least one proximally projecting jet orifice.

13. The thrombectomy catheter of claim 11, wherein the at least one distally projecting jet orifice is circumferentially offset from the at least one proximally projecting jet orifice.

14. The thrombectomy catheter of claim 11, wherein the entrainment inflow orifice is positioned at a distalmost end of the catheter body.

15. A thrombectomy catheter, comprising:

a catheter body extending from a proximal end region to a distal end region and including a catheter lumen extending between the proximal end region and the distal end region;

a high-pressure fluid supply tube extending through the catheter lumen from the catheter body proximal end region toward the catheter body distal end region, the high-pressure fluid supply tube configured for communication with a fluid source near the catheter body proximal end region;

at least one proximally projecting jet orifice extending through a sidewall of the high-pressure fluid supply tube and in communication with a lumen of the high-pressure fluid supply tube, the at least one proximally projecting jet orifice for expelling at least one proximally oriented fluid jet from the lumen of the high-pressure fluid supply tube within the catheter lumen in a generally proximal direction;

at least one distally projecting jet orifice extending through the sidewall of the high-pressure fluid supply tube proximate a distal end of the high-pressure fluid supply tube, the at least one distally projecting jet orifice having a sidewall extending through the sidewall of the high-pressure fluid supply tube from the lumen of the high-pressure fluid supply tube to an exterior of the high-pressure fluid supply tube, the at least one distally projecting jet orifice for expelling at least one distally oriented fluid jet from the lumen of the high-pressure fluid supply tube within the catheter lumen in a generally distal direction; and an entrainment inflow orifice positioned along the catheter body distal end region;

wherein the sidewall of the at least one distally projecting jet orifice extends at an oblique angle to a longitudinal axis of the high-pressure fluid supply tube.

16. The thrombectomy catheter of claim 15, wherein a diameter of the at least one distally projecting jet orifice is less than an inner diameter of the high-pressure fluid supply tube.

* * * * *